(12) United States Patent
Kim et al.

(10) Patent No.: US 9,393,072 B2
(45) Date of Patent: Jul. 19, 2016

(54) MAP AND ABLATE OPEN IRRIGATED HYBRID CATHETER

(71) Applicant: BOSTON SCIENTIFIC SCIMED, INC., Maple Grove, MN (US)

(72) Inventors: Isaac J. Kim, San Jose, CA (US); Josef V. Koblish, Sunnyvale, CA (US); Simplicio A. Velilla, Santa Clara, CA (US); Mark D. Mirigian, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/295,089

(22) Filed: Jun. 3, 2014

(65) Prior Publication Data
US 2014/0288548 A1     Sep. 25, 2014

Related U.S. Application Data

(63) Continuation of application No. 13/859,523, filed on Apr. 9, 2013, now Pat. No. 8,740,900, which is a continuation of application No. 12/821,459, filed on Jun. 23, 2010, now Pat. No. 8,414,579.

(60) Provisional application No. 61/325,456, filed on Apr. 19, 2010, provisional application No. 61/221,967, filed on Jun. 30, 2009.

(51) Int. Cl.
*A61B 18/18* (2006.01)
*A61B 18/14* (2006.01)
(Continued)

(52) U.S. Cl.
CPC .............. *A61B 18/18* (2013.01); *A61B 18/1492* (2013.01); *A61B 5/0422* (2013.01);
(Continued)

(58) Field of Classification Search
CPC ..................... A61B 2018/00011; A61B 18/02; A61B 2018/00839; A61B 2218/002; A61B 2018/00083; A61B 2018/1497
USPC .......................... 600/372–374, 393, 466, 474; 606/20–23, 32–33, 41
See application file for complete search history.

(56) References Cited

U.S. PATENT DOCUMENTS 3,773,401 A   11/1973 Douklias et al.
4,732,149 A    3/1988 Sutter
(Continued)

FOREIGN PATENT DOCUMENTS

CA    2682055 A1   10/2008
CA    2847846 A1    3/2013
(Continued)

OTHER PUBLICATIONS

Goldberg, S. Nahum et al., "Variables Affecting Proper System Grounding for Radiofreguency Ablation in an AnimaL Model", JVIR, vol. 11, No. 8, Sep. 2000, pp. 1069-1075.
(Continued)

*Primary Examiner* — Joseph Stoklosa
*Assistant Examiner* — Brian M Antiskay
(74) *Attorney, Agent, or Firm* — Faegre Baker Daniels LLP

(57) ABSTRACT

An embodiment of an open-irrigated catheter system comprises a tip section, a distal insert, and mapping electrodes. The tip section has an exterior wall that defines an open interior region within the tip section. The exterior wall includes mapping electrode openings and irrigation ports. The exterior wall is conductive for delivering radio frequency (RF) energy for an RF ablation procedure. The irrigation ports are in fluid communication with the open interior region to allow fluid to flow from the open interior region through the irrigation ports. The distal insert is positioned within the tip section to separate the open region into a distal fluid reservoir and a proximal fluid reservoir. The mapping electrodes are positioned in the mapping electrode openings in the tip section.

20 Claims, 11 Drawing Sheets

(51) Int. Cl.
*A61B 10/04* (2006.01)
*A61B 5/042* (2006.01)
*A61B 17/00* (2006.01)
*A61B 18/00* (2006.01)
*A61B 5/00* (2006.01)

(52) U.S. Cl.
CPC .... *A61B 5/7217* (2013.01); *A61B 2017/00084* (2013.01); *A61B 2018/00029* (2013.01); *A61B 2018/00351* (2013.01); *A61B 2018/00577* (2013.01); *A61B 2018/00589* (2013.01); *A61B 2018/00773* (2013.01); *A61B 2018/00839* (2013.01); *A61B 2018/1467* (2013.01); *A61B 2218/002* (2013.01); *Y10T 29/49002* (2015.01); *Y10T 29/49826* (2015.01)

(56) References Cited

U.S. PATENT DOCUMENTS

| | | | |
|---|---|---|---|
| 4,763,660 A | 8/1988 | Kroll et al. | |
| 5,029,588 A | 7/1991 | Yock et al. | |
| 5,154,387 A | 10/1992 | Trailer | |
| 5,178,150 A | 1/1993 | Silverstein et al. | |
| 5,217,460 A | 6/1993 | Knoepfler | |
| 5,238,004 A | 8/1993 | Sahatjian et al. | |
| 5,240,003 A | 8/1993 | Lancee et al. | |
| 5,254,088 A | 10/1993 | Lundquist et al. | |
| 5,295,482 A | 3/1994 | Clare et al. | |
| 5,318,589 A | 6/1994 | Lichtman | |
| 5,324,284 A | 6/1994 | Imran | |
| 5,331,966 A | 7/1994 | Bennett et al. | |
| 5,334,193 A * | 8/1994 | Nardella | 606/41 |
| 5,341,807 A | 8/1994 | Nardella | |
| 5,383,874 A | 1/1995 | Jackson et al. | |
| 5,385,146 A | 1/1995 | Goldreyer | |
| 5,385,148 A | 1/1995 | Lesh et al. | |
| 5,391,199 A | 2/1995 | Ben-Haim | |
| 5,398,683 A | 3/1995 | Edwards et al. | |
| 5,423,811 A * | 6/1995 | Imran et al. | 606/41 |
| 5,447,529 A | 9/1995 | Marchlinski et al. | |
| 5,462,521 A | 10/1995 | Brucker et al. | |
| 5,482,054 A | 1/1996 | Slater et al. | |
| 5,485,849 A | 1/1996 | Panescu et al. | |
| 5,494,042 A | 2/1996 | Panescu et al. | |
| 5,500,012 A | 3/1996 | Brucker et al. | |
| 5,520,683 A | 5/1996 | Subramaniam et al. | |
| 5,571,088 A | 11/1996 | Lennox et al. | |
| 5,573,535 A | 11/1996 | Viklund | |
| 5,579,764 A | 12/1996 | Goldreyer | |
| 5,582,609 A | 12/1996 | Swanson et al. | |
| 5,647,870 A | 7/1997 | Kordis et al. | |
| 5,718,701 A | 2/1998 | Shai et al. | |
| 5,722,402 A | 3/1998 | Swanson et al. | |
| 5,762,067 A | 6/1998 | Dunham et al. | |
| 5,788,636 A | 8/1998 | Curley | |
| 5,800,482 A | 9/1998 | Pomeranz et al. | |
| 5,820,568 A | 10/1998 | Willis | |
| 5,830,213 A | 11/1998 | Panescu et al. | |
| 5,833,621 A | 11/1998 | Panescu et al. | |
| 5,836,990 A | 11/1998 | Li | |
| 5,868,735 A | 2/1999 | Lafontaine | |
| 5,871,483 A | 2/1999 | Jackson et al. | |
| 5,913,856 A * | 6/1999 | Chia et al. | 606/41 |
| 5,916,213 A | 6/1999 | Haissaguerre et al. | |
| 5,919,188 A | 7/1999 | Shearon et al. | |
| 6,004,269 A | 12/1999 | Crowley et al. | |
| 6,027,500 A | 2/2000 | Buckles et al. | |
| 6,050,994 A | 4/2000 | Sherman | |
| 6,059,778 A | 5/2000 | Sherman | |
| 6,064,905 A | 5/2000 | Webster, Jr. et al. | |
| 6,070,094 A | 5/2000 | Swanson et al. | |
| 6,083,170 A | 7/2000 | Ben-Haim | |
| 6,083,222 A | 7/2000 | Klein et al. | |
| 6,099,524 A | 8/2000 | Lipson et al. | |
| 6,101,409 A | 8/2000 | Swanson et al. | |
| 6,116,027 A | 9/2000 | Smith et al. | |
| 6,120,476 A * | 9/2000 | Fung et al. | 604/95.04 |
| 6,165,123 A | 12/2000 | Thompson | |
| 6,171,305 B1 | 1/2001 | Sherman | |
| 6,200,314 B1 | 3/2001 | Sherman | |
| 6,206,831 B1 | 3/2001 | Suorsa et al. | |
| 6,210,337 B1 | 4/2001 | Dunham et al. | |
| 6,216,027 B1 | 4/2001 | Willis et al. | |
| 6,224,557 B1 | 5/2001 | Ziel et al. | |
| 6,233,491 B1 | 5/2001 | Kordis et al. | |
| 6,241,754 B1 | 6/2001 | Swanson et al. | |
| 6,270,493 B1 | 8/2001 | Lalonde et al. | |
| 6,290,697 B1 | 9/2001 | Tu et al. | |
| 6,352,534 B1 | 3/2002 | Paddock et al. | |
| 6,400,981 B1 | 6/2002 | Govari | |
| 6,423,002 B1 | 7/2002 | Hossack | |
| 6,475,213 B1 | 11/2002 | Whayne et al. | |
| 6,488,678 B2 | 12/2002 | Sherman | |
| 6,491,710 B2 | 12/2002 | Satake | |
| 6,508,767 B2 | 1/2003 | Burns et al. | |
| 6,508,769 B2 | 1/2003 | Bonnefous | |
| 6,508,803 B1 | 1/2003 | Horikawa et al. | |
| 6,516,667 B1 | 2/2003 | Broad et al. | |
| 6,517,533 B1 | 2/2003 | Swaminathan | |
| 6,517,534 B1 | 2/2003 | McGovern et al. | |
| 6,537,271 B1 | 3/2003 | Murray et al. | |
| 6,544,175 B1 | 4/2003 | Newman | |
| 6,547,788 B1 | 4/2003 | Maguire et al. | |
| 6,569,162 B2 | 5/2003 | He | |
| 6,572,547 B2 | 6/2003 | Miller et al. | |
| 6,575,966 B2 | 6/2003 | Lane et al. | |
| 6,575,969 B1 | 6/2003 | Rittman et al. | |
| 6,579,278 B1 | 6/2003 | Bencini | |
| 6,582,372 B2 | 6/2003 | Poland | |
| 6,589,182 B1 | 7/2003 | Loftman et al. | |
| 6,592,525 B2 | 7/2003 | Miller et al. | |
| 6,602,242 B1 | 8/2003 | Fung et al. | |
| 6,611,699 B2 | 8/2003 | Messing | |
| 6,620,103 B1 | 9/2003 | Bruce et al. | |
| 6,632,179 B2 | 10/2003 | Wilson et al. | |
| 6,638,222 B2 | 10/2003 | Chandrasekaran et al. | |
| 6,640,120 B1 | 10/2003 | Swanson et al. | |
| 6,647,281 B2 | 11/2003 | Morency | |
| 6,656,174 B1 | 12/2003 | Hegde et al. | |
| 6,658,279 B2 | 12/2003 | Swanson et al. | |
| 6,666,862 B2 | 12/2003 | Jain et al. | |
| 6,671,533 B2 | 12/2003 | Chen et al. | |
| 6,676,606 B2 | 1/2004 | Simpson et al. | |
| 6,689,128 B2 | 2/2004 | Sliwa, Jr. et al. | |
| 6,692,441 B1 | 2/2004 | Poland et al. | |
| 6,702,811 B2 | 3/2004 | Stewart et al. | |
| 6,705,992 B2 | 3/2004 | Gatzke | |
| 6,709,396 B2 | 3/2004 | Flesch et al. | |
| 6,711,429 B1 | 3/2004 | Gilboa et al. | |
| 6,719,756 B1 | 4/2004 | Muntermann | |
| 6,735,465 B2 | 5/2004 | Panescu | |
| 6,736,814 B2 | 5/2004 | Manna et al. | |
| 6,743,174 B2 | 6/2004 | Ng et al. | |
| 6,773,402 B2 | 8/2004 | Govari et al. | |
| 6,776,758 B2 | 8/2004 | Peszynski et al. | |
| 6,795,721 B2 | 9/2004 | Coleman et al. | |
| 6,796,979 B2 | 9/2004 | Lentz | |
| 6,796,980 B2 | 9/2004 | Hall | |
| 6,804,545 B2 | 10/2004 | Fuimaono et al. | |
| 6,805,128 B1 | 10/2004 | Pless et al. | |
| 6,811,550 B2 | 11/2004 | Holland et al. | |
| 6,824,517 B2 | 11/2004 | Salgo et al. | |
| 6,837,884 B2 | 1/2005 | Woloszko | |
| 6,837,886 B2 | 1/2005 | Collins et al. | |
| 6,845,264 B1 | 1/2005 | Skladnev et al. | |
| 6,917,834 B2 | 7/2005 | Koblish et al. | |
| 6,922,579 B2 | 7/2005 | Taimisto et al. | |
| 6,923,808 B2 | 8/2005 | Taimisto | |
| 6,932,811 B2 | 8/2005 | Hooven et al. | |
| 6,945,938 B2 | 9/2005 | Grunwald | |
| 6,950,689 B1 | 9/2005 | Willis et al. | |
| 6,952,615 B2 | 10/2005 | Satake | |
| 6,958,040 B2 | 10/2005 | Oliver et al. | |

(56) References Cited

U.S. PATENT DOCUMENTS

| | | |
|---|---|---|
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,105,122 B2 | 9/2006 | Karason |
| 7,112,198 B2 | 9/2006 | Satake |
| 7,115,122 B1 | 10/2006 | Swanson et al. |
| 7,131,947 B2 | 11/2006 | Demers |
| 7,166,075 B2 | 1/2007 | Varghese et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,278,993 B2 | 10/2007 | Kelly et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,311,708 B2 | 12/2007 | McClurken |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,387,126 B2 | 6/2008 | Cox et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,892,228 B2 | 2/2011 | Landis et al. |
| 7,918,850 B2 | 4/2011 | Govari et al. |
| 8,016,822 B2 | 9/2011 | Swanson |
| 8,128,617 B2 | 3/2012 | Bencini et al. |
| 8,221,409 B2 | 7/2012 | Cao et al. |
| 8,414,579 B2 | 4/2013 | Kim et al. |
| 8,579,889 B2 | 11/2013 | Bencini |
| 8,657,814 B2 | 2/2014 | Werneth et al. |
| 8,740,900 B2 | 6/2014 | Kim et al. |
| 8,894,643 B2 | 11/2014 | Watson et al. |
| 8,945,015 B2 | 2/2015 | Rankin et al. |
| 9,089,340 B2 | 7/2015 | Hastings et al. |
| 9,125,668 B2 | 9/2015 | Subramaniam et al. |
| 9,211,156 B2 | 12/2015 | Kim et al. |
| 2001/0029371 A1 | 10/2001 | Kordis |
| 2002/0087208 A1 | 7/2002 | Koblish et al. |
| 2002/0107511 A1 | 8/2002 | Collins et al. |
| 2003/0004506 A1 | 1/2003 | Messing |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |
| 2004/0082860 A1 | 4/2004 | Haissaguerre |
| 2004/0092806 A1 | 5/2004 | Sagon et al. |
| 2004/0116793 A1 | 6/2004 | Taimisto et al. |
| 2004/0147920 A1 | 7/2004 | Keidar |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0055225 A1 | 3/2007 | Dodd, III et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0270794 A1 | 11/2007 | Anderson et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2008/0300454 A1 | 12/2008 | Goto |
| 2008/0312713 A1 | 12/2008 | Wilfley et al. |
| 2009/0030312 A1 | 1/2009 | Hadjicostis |
| 2009/0048591 A1 | 2/2009 | Ibrahim et al. |
| 2009/0062790 A1 | 3/2009 | Malchano et al. |
| 2009/0062795 A1 | 3/2009 | Vakharia et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |

(56) References Cited

U.S. PATENT DOCUMENTS

| | | |
|---|---|---|
| 2009/0131932 A1 | 5/2009 | Vakharia et al. |
| 2009/0163904 A1 | 6/2009 | Miller et al. |
| 2009/0171341 A1 | 7/2009 | Pope et al. |
| 2009/0182316 A1 | 7/2009 | Bencini |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2010/0010487 A1 | 1/2010 | Phan et al. |
| 2010/0057072 A1 | 3/2010 | Roman et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168831 A1 | 7/2010 | Korivi et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0009857 A1 | 1/2011 | Subramaniam et al. |
| 2011/0022041 A1 | 1/2011 | Ingle et al. |
| 2011/0028820 A1 | 2/2011 | Lau et al. |
| 2011/0028826 A1 | 2/2011 | Kim et al. |
| 2011/0071400 A1 | 3/2011 | Hastings et al. |
| 2011/0071401 A1 | 3/2011 | Hastings et al. |
| 2011/0112569 A1 | 5/2011 | Friedman et al. |
| 2011/0125143 A1 | 5/2011 | Gross et al. |
| 2011/0130648 A1 | 6/2011 | Beeckler et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0224667 A1 | 9/2011 | Koblish et al. |
| 2012/0095347 A1 | 4/2012 | Adam et al. |
| 2012/0101398 A1 | 4/2012 | Ramanathan et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |
| 2012/0310064 A1 | 12/2012 | McGee |
| 2012/0330304 A1 | 12/2012 | Vegesna et al. |
| 2013/0023897 A1 | 1/2013 | Wallace |
| 2013/0066312 A1 | 3/2013 | Subramaniam et al. |
| 2013/0066315 A1 | 3/2013 | Subramaniam et al. |
| 2013/0172715 A1 | 7/2013 | Just et al. |
| 2013/0172742 A1 | 7/2013 | Rankin et al. |
| 2013/0190747 A1 | 7/2013 | Koblish et al. |
| 2013/0197363 A1 | 8/2013 | Rankin et al. |
| 2013/0274582 A1 | 10/2013 | Afonso et al. |
| 2014/0012251 A1 | 1/2014 | Himmelstein et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0107453 A1 | 4/2014 | Maskara et al. |
| 2014/0107636 A1 | 4/2014 | Bencini |
| 2014/0276052 A1 | 9/2014 | Rankin et al. |
| 2015/0011995 A1 | 1/2015 | Avitall et al. |
| 2015/0133914 A1 | 5/2015 | Koblish |
| 2015/0133920 A1 | 5/2015 | Rankin et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374436 A1 | 12/2015 | Subramaniam et al. |
| 2016/0100884 A1 | 4/2016 | Fay et al. |

FOREIGN PATENT DOCUMENTS

| | | |
|---|---|---|
| CA | 2848053 A1 | 3/2013 |
| CN | 1455655 A | 11/2003 |
| CN | 103917185 A | 7/2014 |
| CN | 103987336 A | 8/2014 |
| CN | 104619259 A | 5/2015 |
| CN | 104661609 A | 5/2015 |
| EP | 1343426 B1 | 9/2003 |
| EP | 1343427 B1 | 9/2003 |
| EP | 1502542 A1 | 2/2005 |
| EP | 1547537 A1 | 6/2005 |
| EP | 0985423 B1 | 4/2006 |
| EP | 1690510 A1 | 8/2006 |
| EP | 1717601 A2 | 11/2006 |
| EP | 1935332 A2 | 6/2008 |
| EP | 1343426 B1 | 10/2012 |
| EP | 2755587 A | 7/2014 |
| EP | 2755588 A | 7/2014 |
| EP | 2136702 B1 | 7/2015 |
| JP | 2000000242 A | 1/2000 |
| JP | 200083918 A | 3/2000 |
| JP | 2006239414 A | 9/2006 |
| JP | 2007163559 A | 6/2007 |
| JP | 2007244857 A | 9/2007 |
| JP | 2009142653 A | 12/2008 |
| JP | 2009518150 A | 5/2009 |
| JP | 2010522623 A | 7/2010 |
| JP | 5336465 B2 | 11/2013 |
| JP | 2014012174 A | 1/2014 |
| JP | 2014531244 A | 11/2014 |
| JP | 2015501162 A | 1/2015 |
| JP | 2015509027 A | 3/2015 |
| KR | 20100021401 A | 2/2010 |
| KR | 101490374 B1 | 2/2015 |
| WO | WO9221278 A1 | 12/1992 |
| WO | WO9413358 A1 | 6/1994 |
| WO | WO9419958 A1 | 6/1994 |
| WO | WO9725916 A1 | 7/1997 |
| WO | WO9725917 A1 | 7/1997 |
| WO | WO9736541 A1 | 10/1997 |
| WO | WO9858681 A2 | 12/1998 |
| WO | WO9927862 A1 | 6/1999 |
| WO | WO0029062 A2 | 5/2000 |
| WO | WO0158372 A1 | 8/2001 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO0247569 A1 | 6/2002 |
| WO | WO02102234 A2 | 12/2002 |
| WO | WO2003039338 A2 | 5/2003 |
| WO | WO2007079278 A1 | 7/2007 |
| WO | 2008046031 A2 | 4/2008 |
| WO | WO2008046031 A2 | 4/2008 |
| WO | 2008118992 A1 | 10/2008 |
| WO | WO2008118992 A1 | 10/2008 |
| WO | 2009032421 A2 | 3/2009 |
| WO | WO2009032421 A2 | 3/2009 |
| WO | 2009043824 A1 | 4/2009 |
| WO | WO2009048824 A1 | 4/2009 |
| WO | 2009048943 A1 | 4/2009 |
| WO | 2010054409 A1 | 5/2010 |
| WO | WO2010056771 A1 | 5/2010 |
| WO | 2010082146 A1 | 7/2010 |
| WO | 2011008444 A1 | 1/2011 |
| WO | 2011008681 A1 | 1/2011 |
| WO | 2011033421 A1 | 3/2011 |
| WO | WO2011024133 A1 | 3/2011 |
| WO | 2011089537 A1 | 7/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |

(56) References Cited

FOREIGN PATENT DOCUMENTS

| WO | WO2010001595 | | 1/2012 |
|---|---|---|---|
| WO | WO2010001595 | A1 | 1/2012 |
| WO | WO2012001595 | A1 | 1/2012 |
| WO | WO2012049621 | A1 | 4/2012 |
| WO | WO2012066430 | A1 | 5/2012 |
| WO | 2012161880 | A1 | 11/2012 |
| WO | 2013040201 | A2 | 3/2013 |
| WO | 2013040297 | A1 | 3/2013 |
| WO | 2014072879 | A2 | 5/2014 |
| WO | 2014152575 | A2 | 9/2014 |
| WO | 104640513 | A | 5/2015 |
| WO | 2015143061 | A1 | 9/2015 |
| WO | 2015183635 | A1 | 12/2015 |

OTHER PUBLICATIONS

Haverkamp, W., et. al. Coagulation of Ventricular Myocardium Using Radiofreguency Alternating Current: Bio-Physical Aspects and Experimental Findings, PACE, 12:187-195, Jan. 1989, Part II.
International Preliminary Examination Report issued in PCT/US2013/060183, completed Mar. 24, 2015, 6 pages.
International Preliminary Report on Patentability issued in PCT/US2013/056211, completed Feb. 24, 2015, 5 pages.
International Preliminary Report on Patentability issued in PCT/US2013/060194, mailed Mar. 24, 2015, 6 pages.
International Search Report and Written Opinion issued in PCT/US2008/058324, dated Aug. 18, 2008, 11 pages.
International Search Report and Written Opinion issued in PCT/US2012/031819, mailed Sep. 27, 2012, 16 pages.
International Search Report and Written Opinion issued in PCT/US2012/055309, mailed Nov. 19, 2012, 13 pages.
International Search Report and Written Opinion issued in PCTIUS2012/072061, mailed Mar. 21, 2013, 9 pages.
International Search Report and Written Opinion issued in PCT/US2013/020503, mailed Mar. 20, 2013, 10 pages.
International Search Report and Written Opinion issued in PCT/US2013/021013, mailed Apr. 5, 2013, 14 pages.
International Search Report and Written Opinion issued in PCT/US2013/056211, mailed Jan. 20, 2014
International Search Report and Written Opinion issued in PCT/US2013/060183, mailed Jan. 27, 2014, 10 pages.
International Search Report and Written Opinion issued in PCT/US2013/060194, mailed Jan. 29, 2014.
International Search Report and Written Opinion issued in PCT/US2013/060194, mailed Jan. 29, 2014, 10 pages.
International Search Report and Written Opinion issued in PCT/US2015/021300, mailed Jun. 9, 2015, 11 pages.
International Search Report and Written Opinion issued in PCTUS2015/031591, mailed Aug. 17, 2015, 11 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.

Partial International Search Report issued in PCT/US2012/055155, mailed Dec. 20, 2012, 7 pages.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pires, L, A., et. al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radioirequency Lesions in the Voltage and Frequency Domains", Heart Rhythm 2010, 31st Annual Scientific Sessions, May 12-15 in Denver Colorado.
Ring, E. R., et. al. Catheter Ablation of the Ventricular Septum with Radiofrequency Energy. American Heart Journal, 117(6)1233-1240, Jun. 1989.
Steinke, Karin et al., "Dispersive Pad Site burns With Modern Radiofrequency Ablation Equipment", Surg Laparosc Percutan Tech, vol. 13, No. 6, Dec. 2003, pp. 366-371.
Zachary, J.M. et al., "PO4-86 Pin Electrodes Provide Enhanced Resolution Enabling Titration of Radiofrequency Duration to Lesion Mayuration", Heart Rhythm 2011, 32 Annual Scientific Sessions, May 4-7, San Francisco, CA.
Extended European Search Report issued in EP Application No. 15174537.9, issued Mar. 2, 2016, 7 pages.
International Preliminary Examination Report issued in PCT/US2013/060612, completed Mar. 24, 2015, 10 pages.
International Preliminary Report on Patentability issued in PCT/US2008/058324, mailed Sep. 29, 2009, 9 pages.
International Preliminary Report on Patentability issued in PCT/US2012/055309, issued on Mar. 18, 2014, 8 pages.
International Preliminary Report on Patentabiiity issued in PCT/US2013/058105, completed Mar. 10, 2015.
International Preliminary Report on Patentability issued in PCT/US2014/027491, mailed Sep. 24, 2015, 12 pages.
International Search Report and Written Opinion issued in PCT/US2012/055155, mailed Mar. 11, 2013, 19 pages.
International Search Report and Written Opinion issued in PCT/US2013/058105, mailed Nov. 22, 2013, 16 pages.
International Search Report and Written Opinion issued in PCT/US2013/060612, mailed Feb. 28, 2014, 16 pages.
International Search Report and Written Opinion issued in PCT/US2014/027491, mailed Sep. 23, 2014, 17 pages.
International Search Report and Written Opinion issued in PCT/US2015/055173, mailed Jan. 18, 2016, 11 pages.
International Search Report and Written Opinion issued in PCT/US2015/057242, mailed Jan. 15, 2016, 11 pages.
Invitation to Pay Additional Fees and Partial International Search Report issued in PCT/US2014/027491, mailed Jul. 28, 2014, 5 pages.
Patriciu, A. et al., "Detecting Skin Burns Induced by Surface Electrodes", published in Engineering in Medicine and Biology Society, 2001, Proceedings of the 23rd Annual International Conference of the IEEE, vol. 3, pp. 3129-3131.

\* cited by examiner

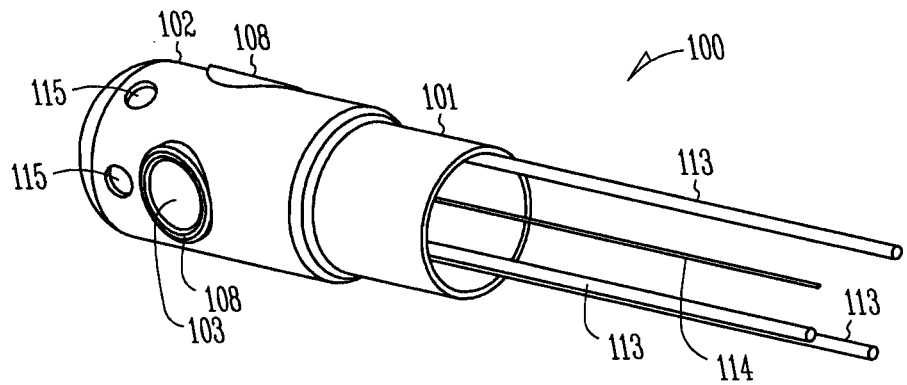
Fig. 1A
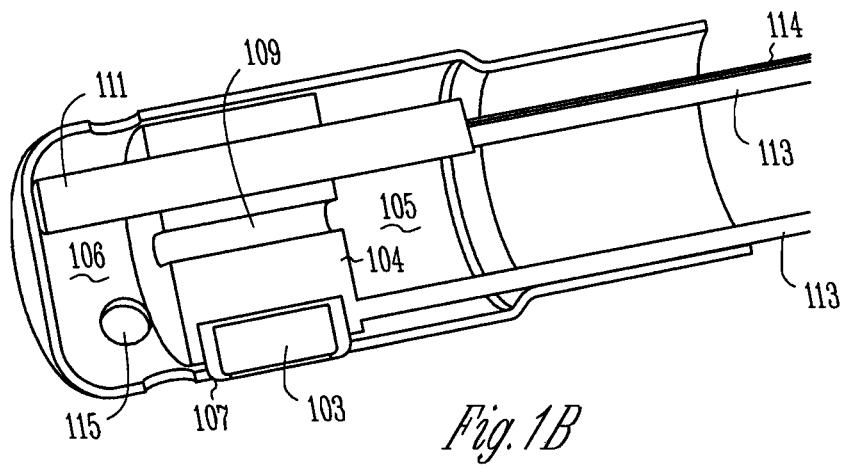
Fig. 1B
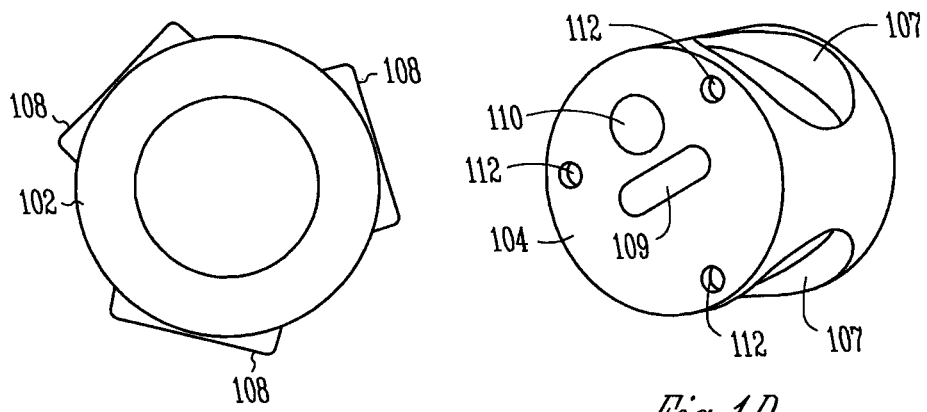
Fig. 1C
Fig. 1D

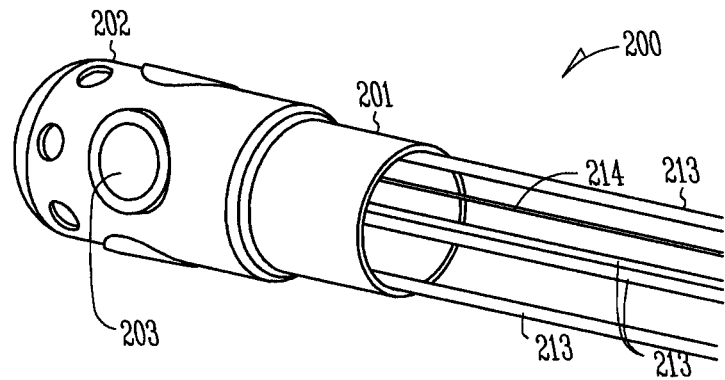
*Fig. 2A*
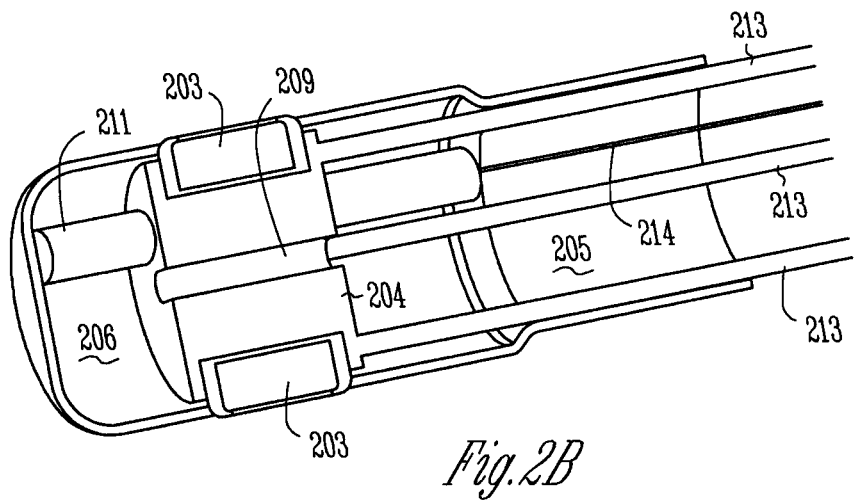
*Fig. 2B*
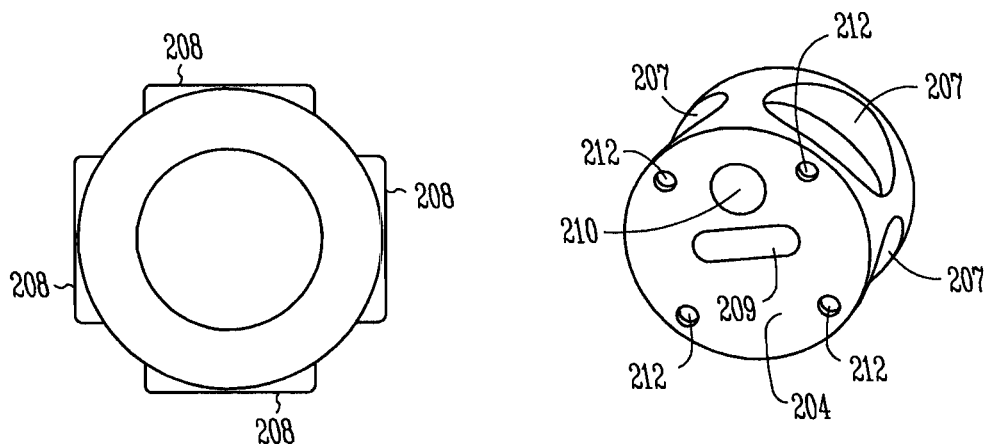
*Fig. 2C*
*Fig. 2D*

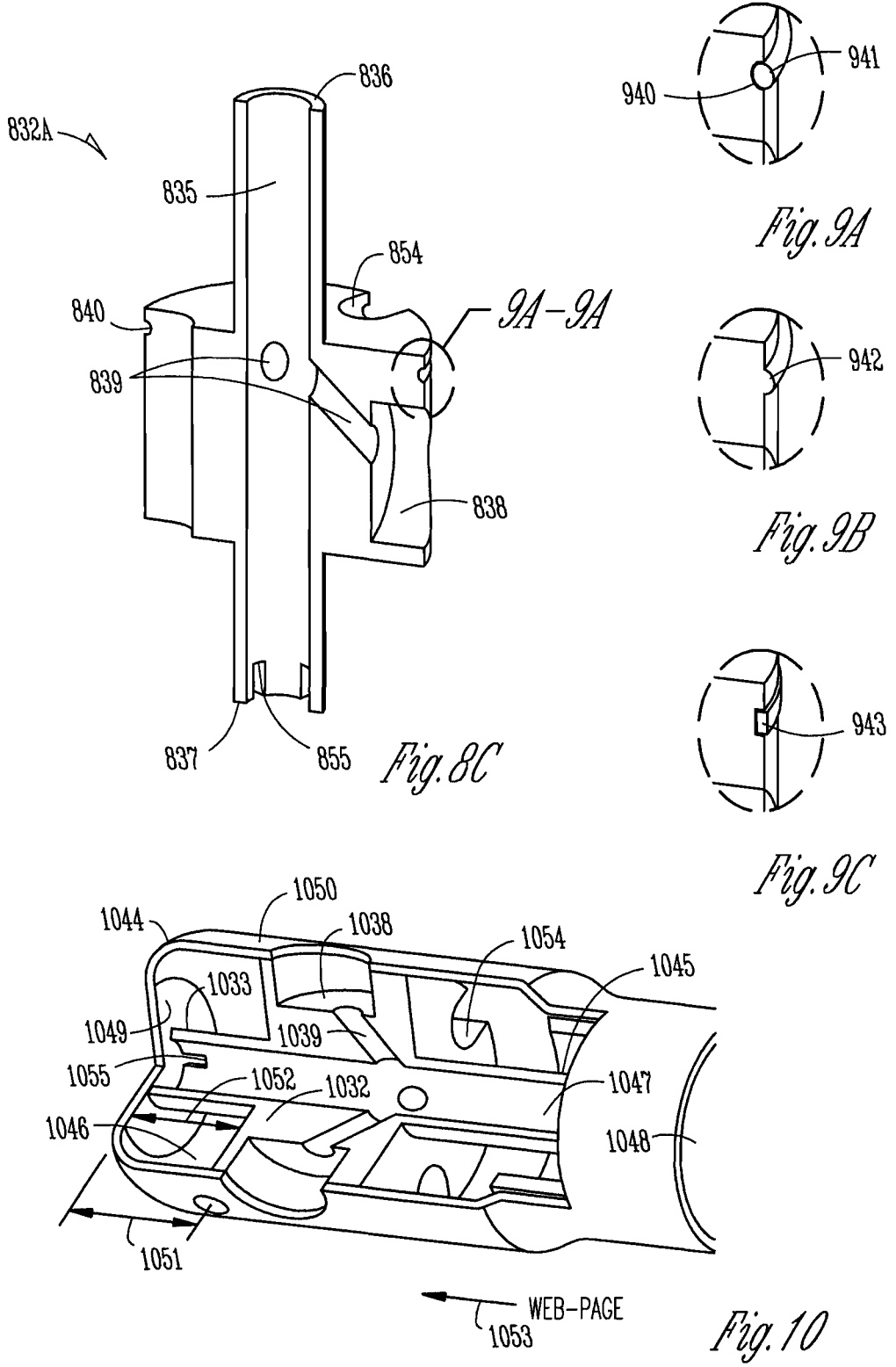

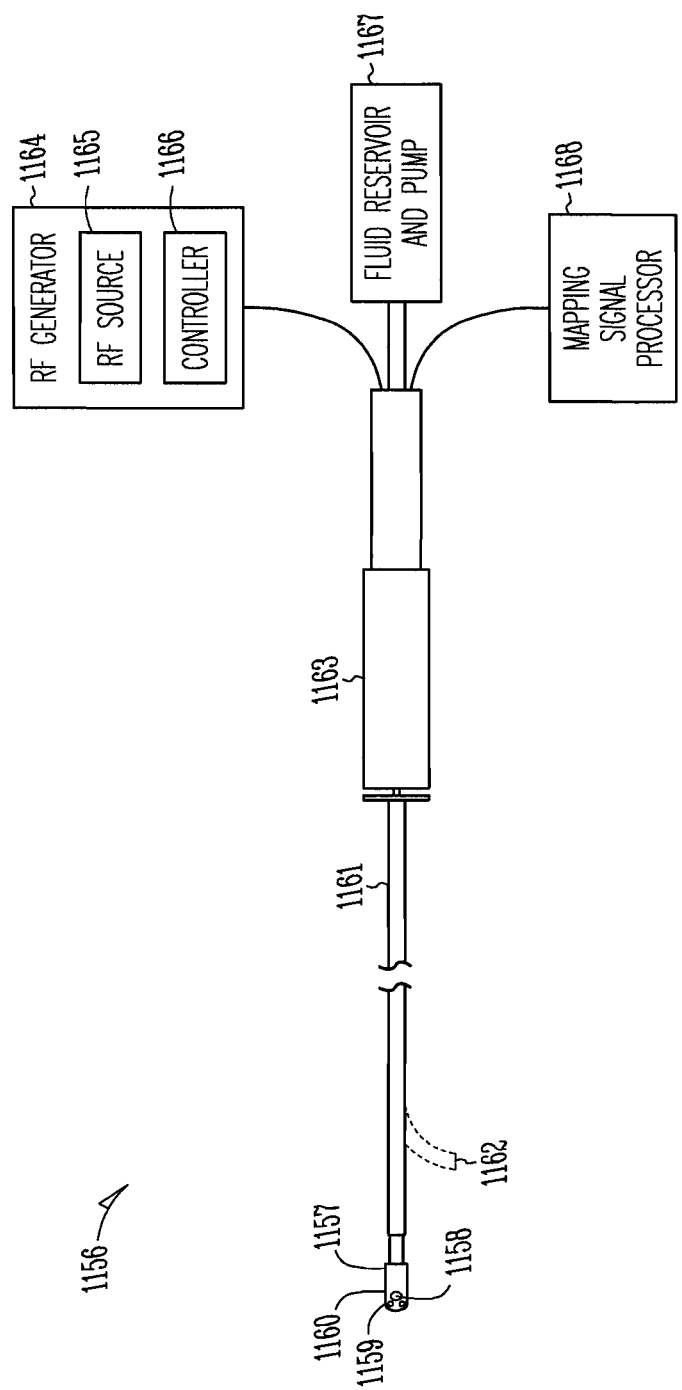

MAP AND ABLATE OPEN IRRIGATED HYBRID CATHETER

CROSS REFERENCE TO RELATED APPLICATIONS

This application is a continuation of U.S. application Ser. No. 13/859,523, filed Apr. 9, 2013, now U.S. Pat. No. 8,740,900; which is a continuation of U.S. application Ser. No. 12/821,459, filed Jun. 23, 2010, now U.S. Pat. No. 8,414,579; which claims the benefit of U.S. Provisional Application No. 61/325,456, filed on Apr. 19, 2010 and U.S. Provisional Application No. 61/221,967, filed on Jun 30, 2009, under 35 U.S.C. §119(e), the entire disclosures of which are incorporated herein by reference.

TECHNICAL FIELD

This application relates generally to medical devices and, more particularly, to systems, devices and methods related to open-irrigated hybrid catheters used to perform mapping and ablation functions.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal contraction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

SUMMARY

An embodiment of an open-irrigated catheter system comprises a tip section, a distal insert, and mapping electrodes. The tip section has an exterior wall that defines an open interior region within the tip section. The exterior wall includes mapping electrode openings and irrigation ports. The exterior wall is conductive for delivering radio frequency (RF) energy for an RF ablation procedure. The irrigation ports are in fluid communication with the open interior region to allow fluid to flow from the open interior region through the irrigation ports. The distal insert is positioned within the tip section to separate the open region into a distal fluid reservoir and a proximal fluid reservoir. The mapping electrodes are positioned in the mapping electrode openings in the tip section.

A catheter system embodiment comprises a conductive exterior wall with mapping electrode openings, wherein the conductive exterior wall is configured for use in delivering RF energy for ablation functions. The catheter system embodiment may, but need not, be an open-irrigated catheter. The catheter system embodiment includes mapping electrodes positioned in the mapping electrode openings, and noise artifact isolators positioned in the mapping electrode openings. The mapping electrodes are electrically insulated from the exterior wall by the noise artifact isolators.

An electrode assembly embodiment comprises an electrode, an electrode shaft, and a noise artifact isolator. The electrode has a circumference defining sides of the electrode, a first surface, and a second surface opposite the first surface. The electrode shaft extends from the second surface of the electrode, and is in electrical conduction with the electrode. The noise artifact isolator is in contact with the sides of the electrode and surrounds the circumference of the electrode.

A method of forming an open-irrigated catheter tip includes inserting a distal insert into a distal tip section and connecting the distal tip section to a proximally adjacent structure. Inserting the distal insert includes moving the distal insert into the distal tip section until a distal extension of the insert contacts a distal end of the distal tip section to self-position the distal insert proximate to irrigation ports.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 1A-1D illustrate an embodiment of a hybrid catheter with distal irrigation ports and three microelectrodes used to perform the mapping function.

FIGS. 2A-2D illustrate an embodiment of a hybrid catheter with distal irrigation ports and four microelectrodes used to perform the mapping function.

FIGS. 8A-8C illustrate various distal insert embodiments configured for self-alignment and configured to isolate electrical components from the irrigation fluid.

FIGS. 9A-9C illustrate various embodiments for realizing a seal area between the distal inserts and the exterior wall of the electrode tip.

FIG. 10 illustrates a section view of a tip electrode assembly embodiment that includes an embodiment of a distal insert.

FIG. 11 illustrates an embodiment of a mapping and ablation system that includes an open-irrigated catheter.

DETAILED DESCRIPTION

Figure 3A:
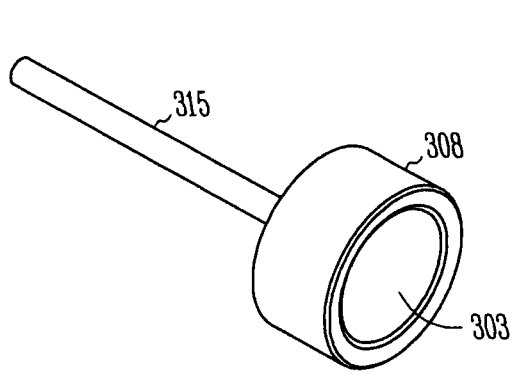
FIGS. 3A-3D illustrate a microelectrode with a noise artifact isolator, according to various embodiments.
Figure 3B:
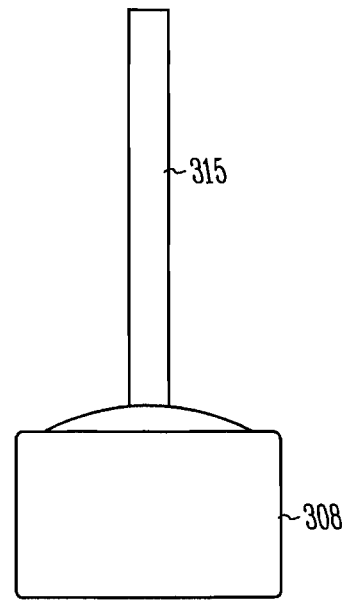
Figure 3C:
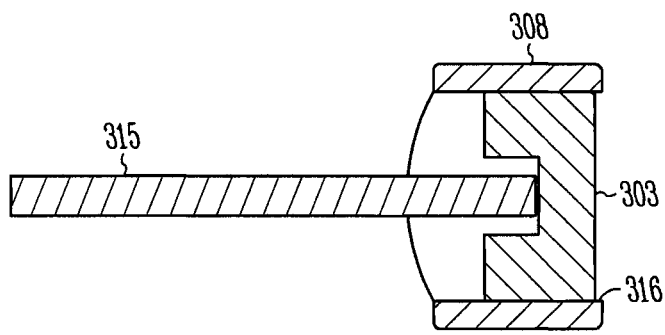
Figure 3D:
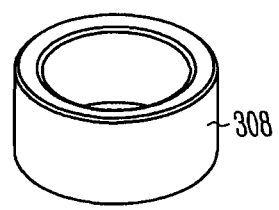

The following detailed description of the present invention refers to subject matter in the accompanying drawings which show, by way of illustration, specific aspects and embodiments in which the present subject matter may be practiced.

These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This present subject matter generally relates to a radiofrequency (RF) ablation catheter system. The catheter is referred to as a hybrid catheter herein as it can be used simultaneously for both localized mapping and ablation functions. The hybrid catheter is configured to provide localized, high resolution ECG signals during ablation. The localized mapping enables the mapping to be more precise than that which can be achieved with conventional ablation catheters. The hybrid catheter has an open-irrigated catheter design. A cooling fluid, such as a saline, is delivered through the catheter to the catheter tip, where the fluid exits through irrigation ports to cool the electrode and surrounding tissue. Clinical benefits of such a catheter include, but are not limited to, controlling the temperature and reducing coagulum formation on the tip of the catheter, preventing impedance rise of tissue in contact with the catheter tip, and maximizing potential energy transfer to the tissue. Additionally, the localized intra cardiac electrical activity can be recorded in real time or near-real time right at the point of energy delivery.

FIGS. 1A-1D illustrate an embodiment of a hybrid catheter with distal irrigation ports and three microelectrodes used to perform the mapping function. The illustrated catheter 100 includes a catheter tip body 101, an open-irrigated tip section 102 used to perform mapping and ablation functions, and mapping electrodes 103. With reference to FIG. 1B, the illustrated embodiment includes a generally hollow tip body and a distal insert 104 disposed therein and configured to separate a proximal fluid reservoir 105 and distal fluid reservoir 106. The hollow tip body has an open interior region defined by an exterior wall of the tip section. Fluid flow through these reservoirs is used to provide targeted cooling of portions of the tip electrode. In the illustrated embodiment, the hollow tip body has a generally cylindrical shape. By way of an example and not limitation, an embodiment of tip body has a diameter on the order of about 0.08-0.1 inches, has a length on the order of about 0.2-0.3 inches, and has an exterior wall with a thickness on the order of 0.003-0.004 inches.

The illustrated distal insert 104 includes openings or apertures 107 sized to receive a microelectrode and its corresponding noise artifact isolator 108. These microelectrodes used in the mapping function to image localized intra cardiac activity. The device may be used to record high resolution, precise localized electrical activity, to prevent excessive heating of the ablation electrode, to allow greater delivery of power, to prevent the formation of coagulum and to provide the ability to diagnose complex ECG activity. The illustrated distal insert 104 also includes a fluid conduit or passage 109 to permit fluid to flow for the proximal fluid reservoir 105 to the distal fluid reservoir 106, a thermocouple opening 110 sized to receive a thermocouple 111, and openings 112 sized to receive electrical conductors 113 used to provide electrical connections to the microelectrodes 103. Also illustrated is a thermocouple wire 114 connected to the thermocouple 111. By way of example and not limitation, an embodiment of the distal insert is fabricated from stainless steel.

The tip section 102 is formed from a conductive material. For example, some embodiments use a platinum-iridium alloy. Some embodiments use an alloy with approximately 90% platinum and 10% iridium. This conductive material is used to conduct RF energy used to form legions during the ablation procedure. A plurality of irrigation ports 115 or exit ports are shown near the distal end of the tip section 102. By way of example and not limitation, an embodiment has irrigation ports with a diameter approximately within a range of 0.01 to 0.02 inches. Fluid, such as a saline solution, flows from the distal fluid reservoir 106, through these ports 115, to the exterior of the catheter. This fluid is used to cool the ablation electrode tip and the tissue near the electrode. This temperature control reduces coagulum formation on the tip of the catheter, prevents impedance rise of tissue in contact with the catheter tip, and increases energy transfer to the tissue because of the lower tissue impedance.

FIGS. 1A-1D illustrate a three microelectrode embodiment in which the three microelectrodes are used to perform mapping functions. However, the hybrid catheter may include other numbers of microelectrodes. For example, FIGS. 2A-2D illustrate an embodiment of a hybrid catheter with distal irrigation ports and four microelectrodes used to perform the mapping function.

The illustrated catheter 200 includes a catheter tip body 201, an open-irrigated tip section 202 used to perform mapping and ablation functions, and microelectrodes 203. With reference to FIG. 1B, the illustrated embodiment includes a generally hollow tip body and a distal insert 204 disposed therein and configured to separate a proximal fluid reservoir 205 and distal fluid reservoir 206. The illustrated distal insert 204 includes openings or apertures 207 sized to receive a microelectrode and its corresponding noise artifact isolator 208. The illustrated distal insert 204 also includes a fluid conduit or passage 209 to permit fluid to flow from the proximal fluid reservoir 205 to the distal fluid reservoir 206, a thermocouple opening 210 sized to receive a thermocouple 211, and openings 212 sized to receive electrical conductors 213 used to provide electrical connections to the microelectrodes 203. Also illustrated is a thermocouple wire 214 connected to the thermocouple 211.

FIGS. 3A-3D illustrate a microelectrode with a noise artifact isolator, according to various embodiments. The illustrated microelectrode 303 is surrounded by the noise artifact isolator 308. An electrode shaft 315 is connected to the electrode 303, and provides an electrical connection between the electrode and the electrical conductors. The microelectrodes are small, independent diagnostic sensing electrodes embedded within the walls of the ablation tip of the RF ablation catheter. The noise artifact isolator electrically isolates the small electrodes from the conductive walls of the ablation tip. According to various embodiments, the noise artifact isolator is a polymer-based material sleeve and/or adhesive that encapsulates the microelectrodes. The isolator has a lip 316 over the outside edge of the microelectrode circumference that blocks the RF pathway into the surface of the microelectrodes. According to various embodiments, the lip extends a distance within a range of approximately 0.002 to 0.020 inches past the surface of the electrode. According to various embodiments, the lip extends a distance of approximately 0.003 inches around the circumference of the microelectrode. The isolator isolates the noise entrance creating a much cleaner electrogram during an RF ablation mode. An in-vitro test result provides evidence that the illustrated isolator significantly reduce the noise artifact during RF. These electrically-isolated microelectrodes are able to sense highly localized electrical activity, avoid a far field component, and simultaneously achieve the ability to ablate tissue without noise artifact during RF mode.

Figure 4A:
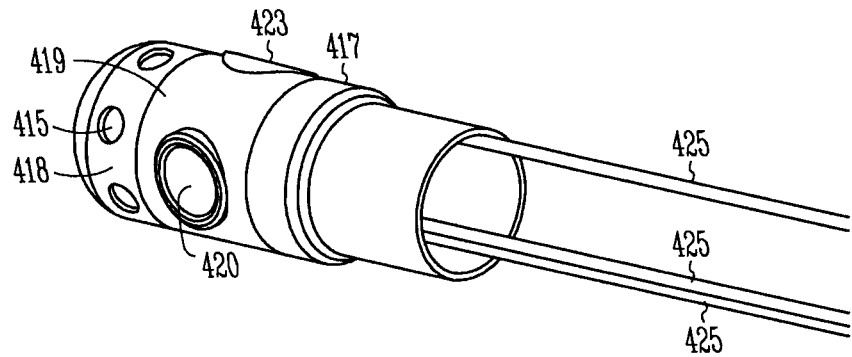
FIGS. 4A-4C illustrate an embodiment of a hybrid catheter in which the tip body includes separate distal and proximal portions, and where both the distal and proximal portions of the tip body are configured to connect to the distal insert that separates the distal and proximal portions.
Figure 4B:
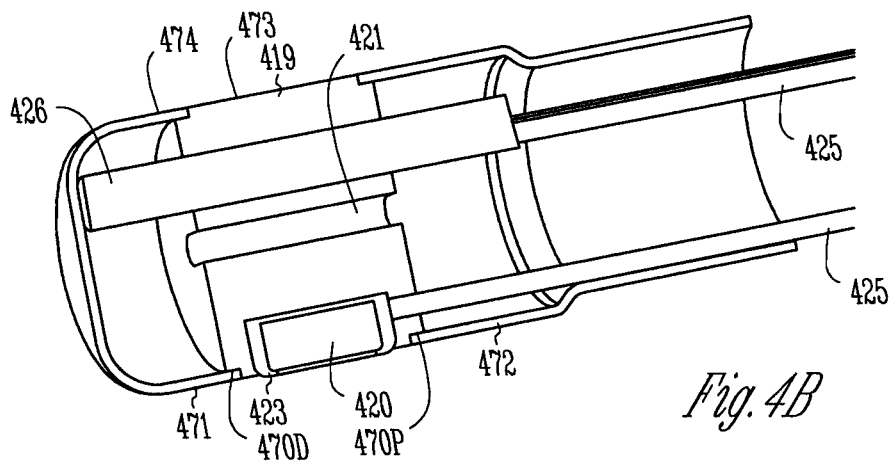
Figure 4C:
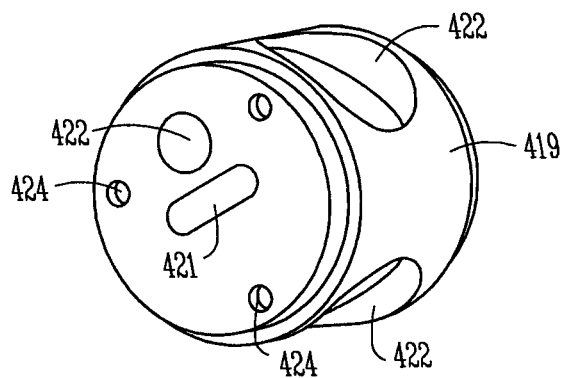

FIGS. 4A-4C illustrate an embodiment of a hybrid catheter in which the tip body includes separate distal and proximal portions, and where both the distal and proximal portions of the tip body are configured to connect to the distal insert that separates the distal and proximal portions. The embodiment illustrated in FIGS. 4A-4C provides a design to simplify manufacturing of the open-irrigated, mapping and ablation catheter. The illustrated device has a distal and proximal chamber separated into proximal 417 and distal tip sections 418. These sections are separated by the distal insert 419, which accommodates microelectrodes 420, a cooling flow channel 421, and a thermocouple slot 422. The illustrated distal insert 419 includes openings or apertures 424 sized to receive a microelectrode and its corresponding noise artifact isolator 423, and openings 424 sized to receive electrical conductors 425 used to provide electrical connections to the microelectrodes 420. The distal tip has distal holes or irrigations ports 415 around the proximal edge of the domed section of the tip.

The illustrated distal insert has ends with distal and proximal lip edges 470D and 470P. Both the distal and proximal tip sections 418 and 417 are designed to fit over the lip edges of the distal insert ends. Specifically, a proximal side 471 of the distal tip section fits over the distal lip 470D and a distal side 472 of the proximal section fits over the proximal kip 470P. A middle portion of the distal insert, between the proximal and distal lips 470P and 470D, has an outer surface 473 substantially flush with an outer surface of the distal and proximal tip sections. In some embodiments, the distal and proximal tips sections are bonded to the distal insert. The bonding process may involve a swaging/mechanical locking method, precise laser welding, force press fit, soldering and other means of chemical/mechanical bonding. The separate tip design provides a simple assembly process to bond the thermocouple and simplifies cleaning of the device. FIG. 4B also illustrates a thermocouple. Thus, according to a method for forming an open-irrigated catheter tip, a distal lip of a distal insert is inserted in a proximal end of the distal tip section. Mapping electrodes are seated in mapping openings around a circumference of the distal insert. A distal end of a proximal tip section is inserted over a proximal lip of the distal insert. A bonding process is performed to bond the distal and proximal tip sections to the distal insert.

Figure 5A:
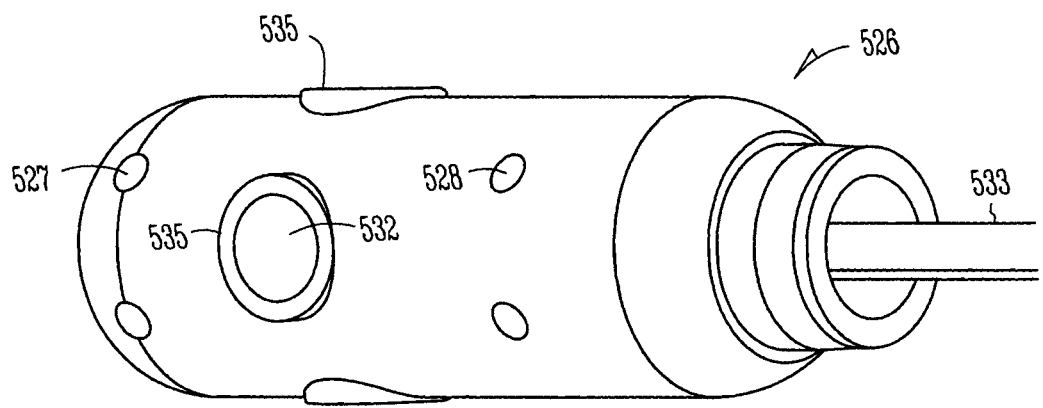
FIGS. 5A-5D illustrate an embodiment of a map and ablate catheter with distal and proximal irrigation ports.
Figure 5B:
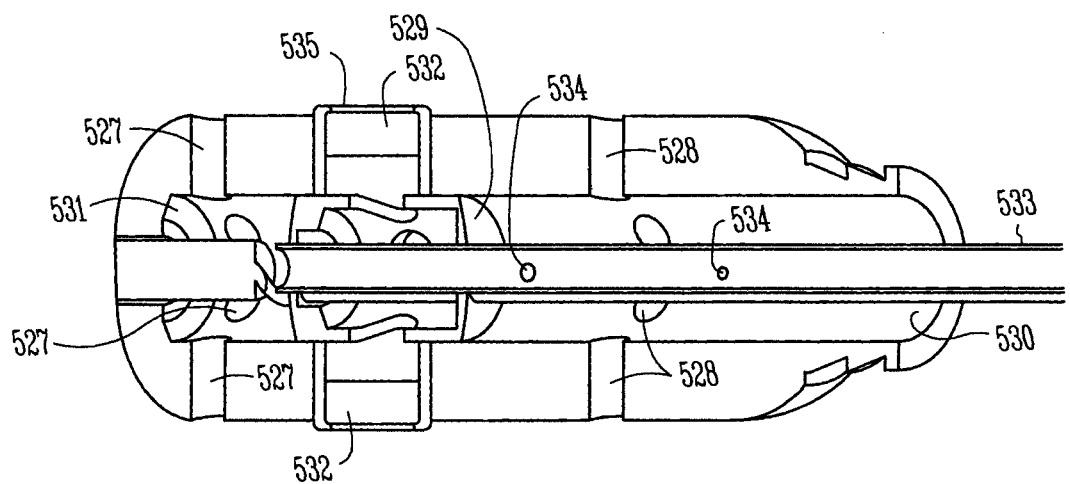
Figure 5C:
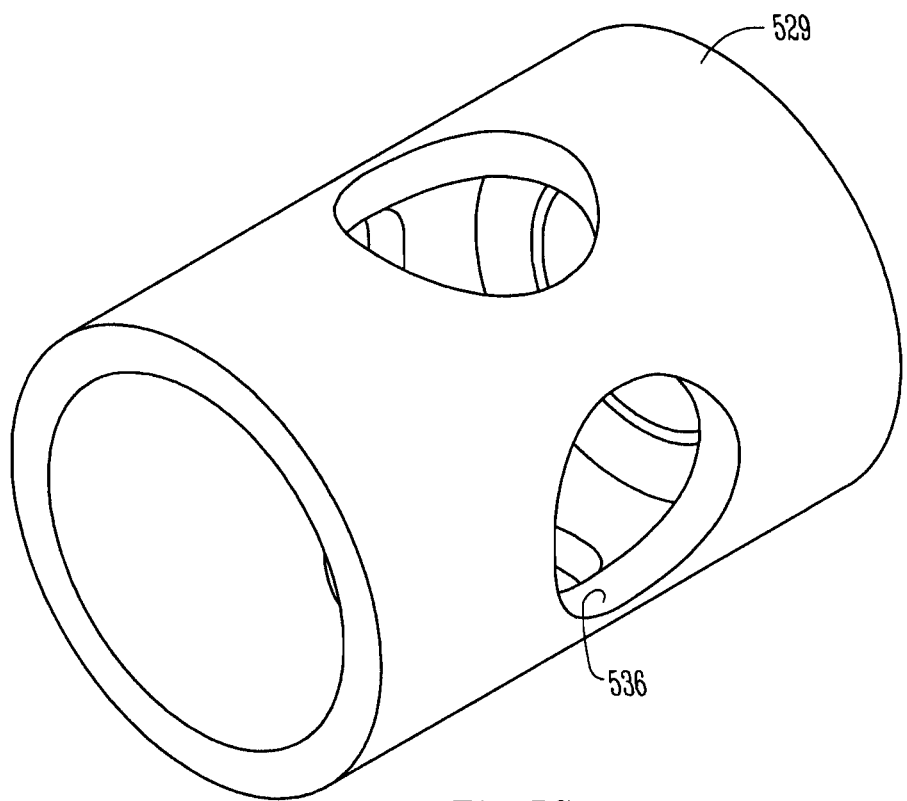

FIGS. 5A-5C illustrate an embodiment of a map and ablate catheter with distal and proximal irrigation ports. The illustrated embodiment provides an open-irrigation RF ablation catheter with mapping and ablation functions in a Blazer tip platform. The Blazer tip is a tip developed by Boston Scientific. The relatively large surface area of the Blazer tip allows more power to be delivered, which hallows a larger lesion to be made. The larger surface area also promotes increased passive cooling by blood over the electrode.

The illustrated catheter has a tip section 526 with distal fluid ports 527, and proximal fluid ports 528. The distal insert 529 is made of plastic components such as Ultem inside the tip which is designed to separate a proximal reservoir 530 and a distal reservoir 531 for targeted cooling portions of the tip electrode, provide openings for the cooling fluid and the thermocouple, and provide housing for the microelectrodes 532 to image real time localized intra cardiac activity. The ends of this distal insert are encapsulated with adhesives to completely isolate distal tip chamber from proximal tip chamber.

The cooling lumen 533 is designed to cool the proximal/distal chamber while insulating the microelectrode lead wire junction from cooling fluid. The cooling lumen 533 includes several micro holes 534 in the proximal area of the tip to allow fluid to pass through these micro holes 534 and through the distal end of the cooling lumen, cooling the proximal tip and ultimately exiting through the proximal tip holes 528. The cooling lumen and tip ports can be configured in different modes to optimize cooling efficiency for both distal and proximal chamber. For example, different diameter sizes and orientations can be implemented to adjust cooling.

Some embodiments include a three microelectrode configuration and some embodiments include a four microelectrode configuration. FIG. 5C illustrates a distal insert 529 for a four microelectrode configuration. The illustrated insert 529 has openings 536 through which an electrical connection can be made with the microelectrodes 532. The tip size is within a range of approximately 4-10 mm, for example. Some embodiments do not include a proximal cooling chamber. The microelectrodes 532, which are used in the mapping function, are isolated from the conductive tip used to perform the ablation using a noise artifact isolator 535.

Figure 5D:
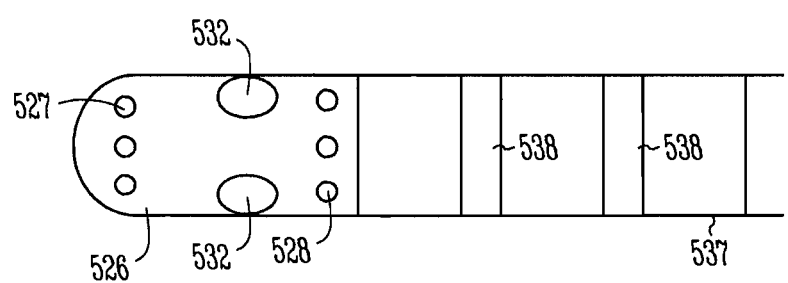

FIG. 5D illustrates an embodiment of the present subject matter incorporated into a Blazer tip. The illustrated embodiment includes a catheter body 537 and a tip section 526, and includes a plurality of ring electrodes 538, the microelectrodes 532, distal fluid ports 527 and proximal fluid ports 528.

Figure 6A:
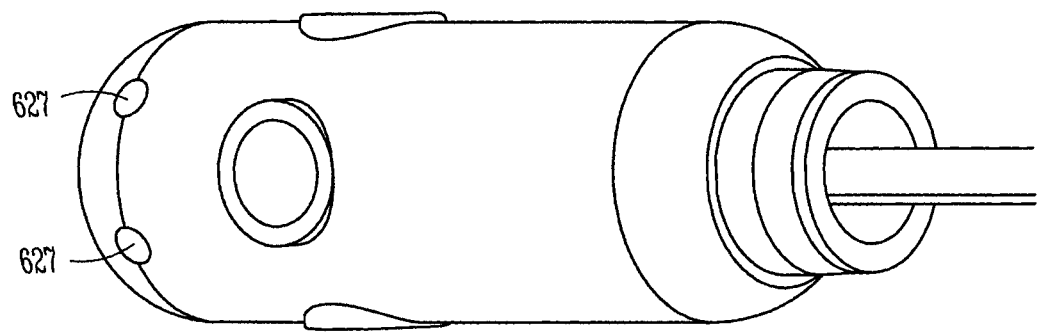
FIGS. 6A-6B illustrate an embodiment of a map and ablate catheter with distal irrigation ports.
Figure 6B:
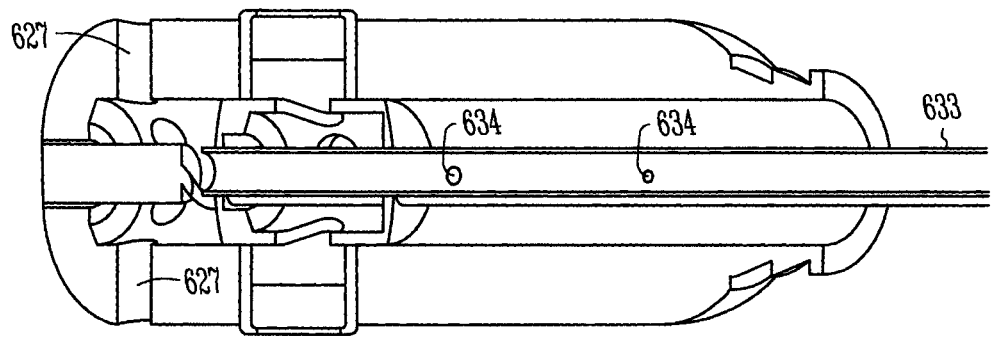

FIGS. 6A-6B illustrate an embodiment of a map and ablate catheter with distal irrigation ports 627. The cooling lumen 633 includes micro holes 634 to pass fluid in a proximal reservoir to cool the proximal portion of the tip. This fluid passes into the distal reservoir out through the distal fluid ports 627.

Figure 7A:
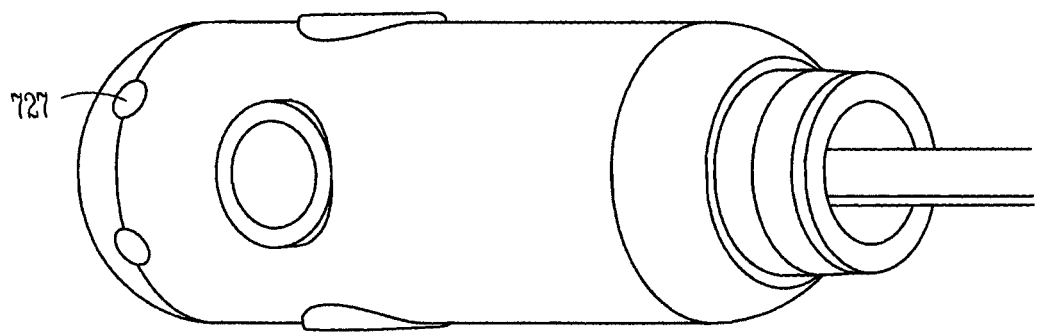
FIGS. 7A-7B illustrate another embodiment of a map and ablate catheter with distal irrigation ports and a proximal fluid chamber.
Figure 7B:
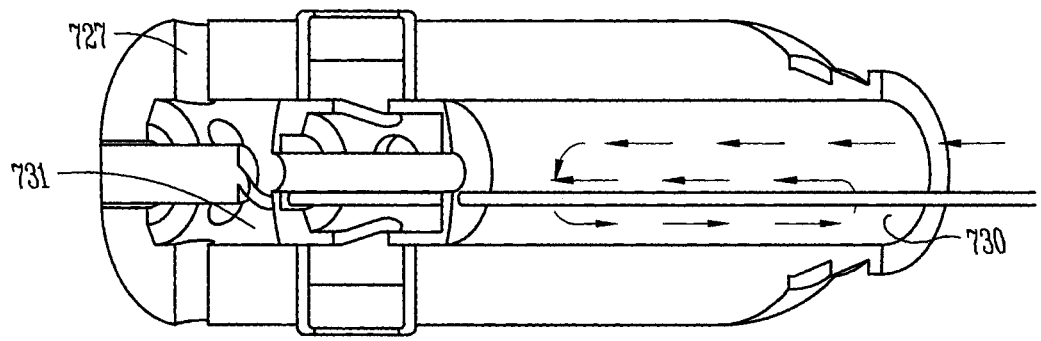

Some embodiments shorten the cooling lumen up to the proximal end of the distal insert, allowing the fluid to cool the proximal end of the chamber before passing the distal tip chamber and ultimately passing thru the distal tip holes. FIGS. 7A-7B illustrate an example of a map and ablate catheter with distal irrigation ports 727 and a proximal fluid chamber, where fluid exits a cooling lumen into a proximal reservoir 730 before passing into the distal reservoir 731 and exiting the distal irrigation ports 727.

Electrical signals, such as electrocardiograms (ECGs), are used during a cardiac ablation procedure to distinguish viable tissue from not viable tissue. If ECG amplitudes are seen to attenuate during the delivery of RF energy into the tissue, the delivery of RF energy into that specific tissue may be stopped. However, noise on the ECG signals makes it difficult to view attenuation. It is currently believed that internal cooling fluid circulation, cooling fluid circulating externally in contact with other electrodes, and/or fluid seepage in between the electrodes and their housing may cause the noise on this type of ablation catheter.

Various embodiments, as described below, isolate the microelectrode signal wires from the cooling fluid circulating in the proximal chamber of the hollow ablation electrode, and thus are expected to reduce the noise that is contributed from the internal cooling fluid circulation. The fluid seal can be provided without bonding or adhesive. The electrical components within the tip are isolated from the cooling flow of irrigation fluid while the irrigation fluid maintains internal cooling of the proximal and distal portions of the tip electrode. Further, as provided in more detail below, these designs have the potential of increasing the accuracy of the temperature readings from the thermocouple.

Various distal insert embodiments include design elements configured for self-positioning the distal insert during manufacturing. These embodiments reduce the number of processing steps to join the distal insert to the tip electrode.

Figure 8A:
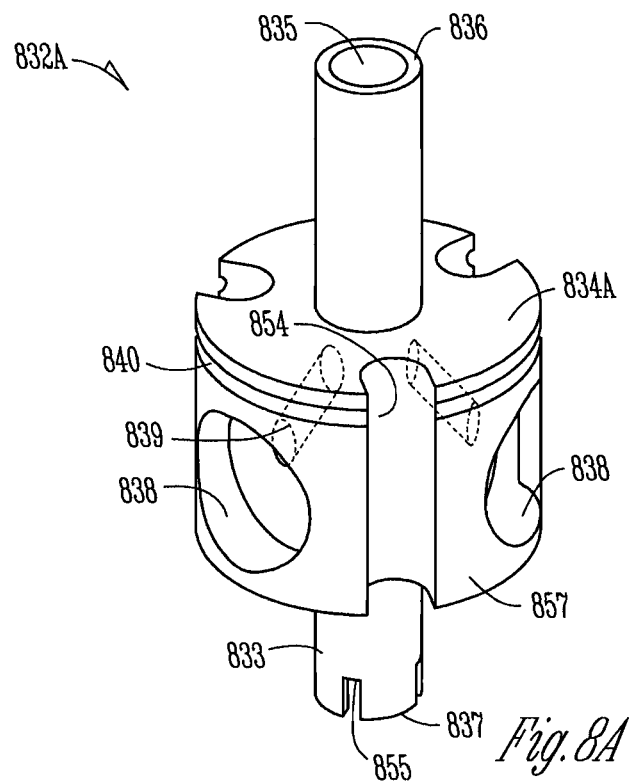
Figure 8B:
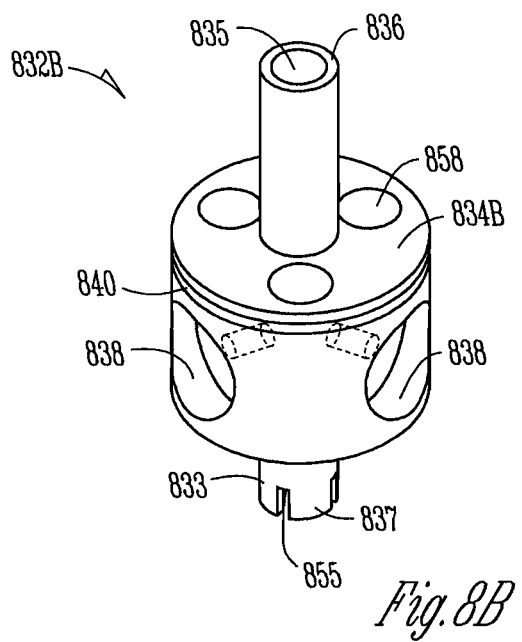

FIGS. 8A-8C illustrate various distal insert embodiments configured for self-alignment and configured to isolate electrical components from the irrigation fluid. Some embodiments are configured for self-alignment, some embodiments are configured to isolate electrical components from the irrigation fluid, and some embodiments as illustrated are configured for both self-alignment and for isolating electrical components from the irrigation fluid. FIG. 8A illustrates a distal insert embodiment with fluid channels formed in a peripheral surface of the insert, FIG. 8B illustrates a distal insert embodiment with fluid lumens formed through the distal insert, and FIG. 8C illustrates a section view of the distal insert embodiment of FIG. 8A.

The illustrated distal inserts 832A and 832B include a distally-extending member 833. The distal insert includes a main body portion 834A and 834B and a channel 835 extending from a proximal channel end 836 through the main body portion to a distal channel end 837. The main body portion 834A and 834B has a circumference or outer diameter generally complementary to an inside diameter of the exterior wall of the tip section, and has a peripheral surface with openings 838 therein sized to receive the electrodes. The exterior wall of the tip section also has mapping electrode apertures. During assembly, the apertures in the exterior wall and the apertures in the distal insert are aligned, and the mapping electrodes are positioned and potted within the apertures. The channel has an interior passage that is isolated from the proximal fluid reservoir. Mapping electrode wires extend through the interior passage of the channel into smaller channels 839 in the main body portion of the distal insert to the mapping electrodes.

The distal insert embodiments illustrated in FIGS. 8A-8C include a circumferential groove 840, on which an o-ring is seated to form a seal between the distal insert and the exterior wall of the hollow electrode to prevent fluid from seeping around the side of the distal insert. This seal, generally illustrated in FIG. 8C as a seal area, prevents fluid from seeping between the distal insert and the exterior wall of the tip section, and between the electrodes and their housing.

FIGS. 9A-9C illustrate various embodiments for realizing a seal area between the distal inserts and the exterior wall of the electrode tip. FIG. 9A generally illustrates the groove 940 and o-ring 941, such as was generally illustrated in FIGS. 8A-8C. Other embodiments include annular or circumferential detents 942 formed as part of the main body and configured to extend away from the peripheral surface of the main body, as generally illustrated in FIG. 9B. These detents engage the interior surface of the exterior wall of the tip section, thus securing the distal insert within the tip section. Some embodiments, as generally illustrated in FIG. 9C, form the peripheral surface with a circumferential gasket 943 configured to provide a seal between the distal insert and the exterior wall. The gasket 943 may be formed from a flexible material such as a polymer. These embodiments for realizing a seal are not intended to be an exclusive list, as other seals may be used to seal the fluid from the mapping electrodes.

FIG. 10 illustrates a section view of a tip electrode assembly embodiment 1044 that includes an embodiment of a distal insert 1032. The distal insert partitions a hollow ablation electrode into a proximal chamber 1045 and a distal chamber 1046, thus allowing cooling of the proximal chamber 1045. The cooling of the proximal chamber 1045 mitigates heating known as "edge effect" before the fluid is directed into the distal chamber 1046 and discharged through irrigation ports into the vasculature. The distal insert houses multiple, smaller electrodes in apertures 1038 in the tip electrode to provide localized electrical information.

The illustrated embodiment simplifies and improves the consistency of the method for positioning the insert into the hollow tip electrode. The distal insert 1032 is inserted into the hollow tip electrode 1044 and is automatically located within the electrode due to the distally-extending member 1033 of the isolation channel. The outer diameter of the insert and the o-ring are designed such that no additional adhesive is necessary to form a seal between the tip and the distal insert. The proximal section 1047 of the isolation channel terminates in a slot of the adjacent component 1048 that is potted with adhesive.

The exterior wall of the tip section has a distal end 1049 separated from the irrigation ports 1050 of the electrode by a predetermined distance 1051, and the distally-extending member is configured with a predetermined length 1052 to position the distal insert in the tip section on a proximal side of the irrigation ports 1050 when the distal channel end abuts the distal end of the exterior wall of the electrode.

When the apparatus is inserted into a hollow tip electrode in the direction illustrated by arrow 1053, the distal section of the isolated channel has a length that positions the distal edge of the insert above or proximal to the irrigation ports, allowing the irrigation ports provide fluid communication between the distal chamber and the exterior of the ablation electrode.

The overall diameter of the apparatus is similar enough to the inside diameter of the tip electrode that an o-ring placed in the circumferential groove provides an adequate seal forcing cooling fluid to flow through the fluid channels 1054, also illustrated in FIG. 8A at 854. Because of the design characteristics, manufacturing processes are reduced. The channel houses the thermocouple and signal wires from the microelectrodes. The proximal end of the insulated channel terminates in the adjacent structure within the tip, which is potted with epoxy and isolated from the cooling fluid. The thermocouple is in contact with the distal end of the electrode tip. Some embodiments provide slots 1055 at the distal channel end of the channel allowing cooling fluid to circulate into contact with the thermocouple. Some embodiments do not include slots, but rather provide a fluid-tight seal between the channel and the distal end of the electrode tip, such that the fluid does not circulate into contact with the thermocouple.

RF generators are configured with a cut-off temperature, where the RF ablation energy is cut off if the temperature reaches a particular level. However, some RF generators are configured with a relatively low cut-off temperature that reflects a less-than-accurate temperature measurement. The slots 1055 are believed to allow the embodiments of the present subject matter to operate with such devices. Various embodiments provide four slots. Other embodiments include other numbers of slots. Embodiments that include a slotted channel seal the channel at a more proximate position to prevent fluid from traveling through the channel toward the wiring. Some embodiments do not include slots, but rather seal the distal channel end to the distal wall of the electrode to prevent fluid from contacting the thermocouple. Such embodiments that isolate the thermocouple are believed to provide more accurate temperature measurements.

The distal insert includes fluid paths from the proximal chamber to the distal chamber to create a back pressure as fluid enters the proximal chamber, causing the fluid to circulate before being forced through the channels into the distal chamber. According to various embodiments, the fluid paths have an equal cross-sectional area and equally positioned around the center of the distal insert. Various embodiments include three equally-spaced fluid paths. In some embodiments, the fluid paths are fluid channels 856 formed in a peripheral surface 857 of the main body of the distal insert. The fluid channels provide the fluid pathways toward the exterior of the distal insert, thus allowing the insert to seat more electrodes around its circumference. In some embodiments, the fluid paths are lumens 858 formed through the main body of the distal insert. The lumens 858 provide further isolation of the mapping electrodes from the fluid, as the fluid flowing through the lumens is not in contact with the interface between the peripheral surface of the insert and the inner surface of the exterior wall of the electrode.

Wire channel branches, illustrated at 839 in FIG. 8C and at 1039 in FIG. 10, allow the signal wires from the microelectrodes to enter the isolated channel. The illustrated embodiment is designed with three equally-spaced microelectrodes. Thus, the distal electrode embodiment includes three wire channels extending from an electrode aperture in the distal insert to the wire channel. According to various embodiments, these channel branches are angled (e.g. 15 to 60 degrees) to aid wire threading. This entire section is potted with adhesive to isolate this section from any potential cooling fluid.

FIG. 10 also generally illustrates a method for forming an open-irrigated catheter tip. A distal insert 1032 is inserted into a distal tip section or hollow electrode 1044. The distal insert includes a distal extension and the distal tip section includes a distal end and irrigation ports separated from the distal end by a predetermined distance. Inserting the distal insert includes moving the distal insert into the distal tip section until the distal extension contacts the distal end of the distal tip section to self-position the distal insert proximate to the irrigation portions. The distal tip section is connected to a proximally adjacent structure. For example, some embodiments swage the distal tip section to join the distal tip section against the proximally adjacent structure 1044. The distal insert partitions the distal tip section into a distal fluid reservoir between the distal insert and the distal end, and a proximal fluid reservoir between the distal insert and the proximally adjacent structure. The distal insert provides fluid communication between the distal and proximal fluid reservoirs. In various embodiments, inserting the distal insert into the distal tip section includes aligning mapping electrode apertures in the distal insert with mapping electrode apertures in the distal tip section. The mapping electrodes are seated into the mapping electrode apertures. Wires connected to the mapping electrodes run through the channel of the distal insert.

FIG. 11 illustrates an embodiment of a mapping and ablation system 1156 that includes an open-irrigated catheter. The illustrated catheter includes an ablation tip 1157 with mapping microelectrodes 1158 and with irrigation ports 1159. The catheter can be functionally divided into four regions: the operative distal probe assembly region (e.g. the distal portion of catheter body 1160), a main catheter region 1161, a deflectable catheter region 1162, and a proximal catheter handle region where a handle assembly 1163 including a handle is attached. A body of the catheter includes a cooling fluid lumen and may include other tubular element(s) to provide the desired functionality to the catheter. The addition of metal in the form of a braided mesh layer sandwiched in between layers of plastic tubing may be used to increase the rotational stiffness of the catheter.

The deflectable catheter region 1162 allows the catheter to be steered through the vasculature of the patient and allows the probe assembly to be accurately placed adjacent the targeted tissue region. A steering wire (not shown) may be slidably disposed within the catheter body. The handle assembly may include a steering member such as a rotating steering knob that is rotatably mounted to the handle. Rotational movement of the steering knob relative to the handle in a first direction may cause a steering wire to move proximally relative to the catheter body which, in turn, tensions the steering wire, thus pulling and bending the catheter deflectable region into an arc; and rotational movement of the steering knob relative to the handle in a second direction may cause the steering wire to move distally relative to the catheter body which, in turn, relaxes the steering wire, thus allowing the catheter to return toward its form. To assist in the deflection of the catheter, the deflectable catheter region may be made of a lower durometer plastic than the main catheter region.

The illustrated system 1156 includes an RF generator 1164 used to generate the energy for the ablation procedure. The RF generator 1164 includes a source 1165 for the RF energy and a controller 1166 for controlling the timing and the level of the RF energy delivered through the tip 1157. The illustrated system 1156 also includes a fluid reservoir and pump 1167 for pumping cooling fluid, such as a saline, through the catheter and out through the irrigation ports 1159. A mapping signal processor 1168 is connected to the electrodes 1158, also referred to herein as microelectrodes. The mapping signal processor 1168 and electrodes 1158 detect electrical activity of the heart. This electrical activity is evaluated to analyze an arrhythmia and to determine where to deliver the ablation energy as a therapy for the arrhythmia. One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An open-irrigated catheter system for performing mapping and ablation functions, comprising: a tip section having an exterior wall that defines an open interior region within the tip section, wherein the exterior wall includes a plurality of mapping electrode openings, wherein at least one of the mapping electrode openings is spaced apart from a distal end of the exterior wall of the tip section, wherein the exterior wall includes at least one irrigation port in fluid communication with the open interior, and wherein the exterior wall is conductive for delivering radio frequency (RF) energy for an RF ablation procedure; a distal insert positioned within the tip section separating the open interior region into a distal fluid reservoir and a proximal fluid reservoir; a fluid path extending through the open interior region and in fluid communication with the distal fluid reservoir, the proximal fluid reservoir, and at least one irrigation port; a plurality of mapping electrodes seated in the distal insert and aligned with the mapping electrode openings in the tip section; wherein the distal insert has a peripheral surface with openings therein sized to receive at least one insulating element, wherein the distal insert includes at least one insulating element electrically insulating the mapping electrodes from the fluid path, the at least one insulating element including at least one insulated channel configured to electrically insulated wires extending from the plurality of mapping electrodes from the fluid path.

2. The system of claim 1, wherein each mapping electrode has a peripheral surface extending transverse to a longitudinal axis of the tip section, an inner surface facing the open interior region, and an outer surface facing laterally away from the tip section, wherein each insulating element covers the peripheral surface and the inner surface of its corresponding mapping electrode.

3. The system of claim 1, wherein the distal insert defines a fluid conduit extending from the distal fluid reservoir to the proximal fluid reservoir.

4. The system of claim 1, wherein the at least one irrigation port in fluid communication with the open interior region includes at least one distal irrigation port in fluid communication with the distal fluid reservoir.

5. The system of claim 1, wherein the at least one irrigation port in fluid communication with the open interior region includes at least one proximal irrigation port in fluid communication with the proximal fluid reservoir.

6. The system of claim 1, wherein the at least one irrigation port in fluid communication with the open interior region includes at least one distal irrigation port in fluid communication with the distal fluid reservoir and at least one proximal irrigation port in fluid communication with the proximal fluid reservoir.

7. The system of claim 1, further comprising a fluid cooling lumen extending through the distal insert to deliver fluid to the distal fluid reservoir, the fluid cooling lumen having a wall with openings therein to deliver fluid to the proximal fluid reservoir.

8. The system of claim 1, wherein:
the tip section includes a proximal section and a distal section, the proximal section including a distal side, and the distal section including a proximal side;
the distal insert includes a proximal lip on a proximal end of the distal insert and a distal lip on a distal end of the distal insert;
the proximal side of the distal section fits over the distal lip; and the distal side of the proximal section fits over the proximal lip.

9. The system of claim 8, wherein the distal insert includes a middle portion between the proximal and distal lips, the middle portion having an outer surface substantially flush with an outer surface of the proximal section and with an outer surface of the distal section.

10. The system of claim 1, wherein:
the at least one irrigation port is separated from the distal end of the exterior wall of the tip section by a predetermined distance; and
the distal insert includes a distally-extending member terminating in a distal channel end, wherein the distally-extending member is configured with a first predetermined length to position the distal insert in the tip section on a proximal side of the at least one irrigation port when the distal channel end of the distally-extending member abuts the distal end of the exterior wall.

11. The system of claim 1, wherein:
the at least one irrigation port is separated from the distal end of the exterior wall of the tip section by a predetermined distance;
the distal insert includes a main body portion and at least one of the insulated channel extending from a proximal channel end through the main body portion to a distal channel end, the main body portion having a circumference generally complementary to an inner diameter of the exterior wall;
the distal channel end abuts a distal wall of the tip section, the main body is positioned on a proximal side of the at least one irrigation port, and the proximal channel end is connected to a proximally adjacent structure;
the insulated channel has an interior passage that is isolated insulated from the proximal fluid reservoir; and
the system includes wires extending through the interior passage of the insulated channel into the main body portion of the distal insert to the mapping electrodes.

12. The system of claim 1, further comprising a thermocouple.

13. The system of claim 1, wherein the at least one insulating element has a generally annular shape.

14. The system of claim 1, wherein the mapping electrodes include three mapping electrodes approximately equally spaced from each other about a circumference of the tip section.

15. The system of claim 1, wherein the mapping electrodes include four mapping electrodes approximately equally spaced from each other spaced about a circumference of the tip section.

16. An open-irrigated catheter system for performing mapping and ablation functions, comprising: a tip section having an exterior wall that defines an open interior region within the tip section, wherein the exterior wall includes a plurality of mapping electrode openings in fluid communication with the open interior, wherein at least one of the mapping electrode openings is spaced apart from a distal end of the exterior wall of the tip section, wherein the exterior wall includes at least one irrigation port in fluid communication with the open interior region and wherein the exterior wall is conductive for delivering radio frequency (RF) energy for an RF ablation procedure; a distal insert within the tip section separating the open interior region into a distal fluid reservoir and a proximal fluid reservoir; a fluid path extending through the tip section and in fluid communication with the at least one irrigation port; a plurality of mapping electrodes seated in the distal insert and in alignment with the mapping electrode openings in the tip section, wherein each mapping electrode has a peripheral surface extending transverse to a longitudinal axis of the tip section, an inner surface facing the interior of the tip section, and an outer surface facing laterally away from the tip section; wherein the distal insert includes at least one insulating element electrically insulating the mapping electrodes from the fluid path, wherein each insulating element cover the peripheral surface and the inner surface of its corresponding mapping electrode, wherein the at least one insulating element includes at least on insulated channel configured to electrically insulate wires extending from the plurality of mapping electrodes from the fluid path.

17. The system of claim 16, further comprising a distal insert positioned within the tip section separating the open interior region into a distal fluid reservoir and a proximal fluid reservoir, wherein the distal insert has a peripheral surface with openings therein sized to receive the at least one insulating element.

18. The system of claim 16, wherein the insulating elements extend outward from the exterior wall past an outside surface of the mapping electrodes.

19. An open-irrigated catheter system for performing mapping and ablation functions, comprising:
a tip section having an exterior wall that defines an open interior region within the tip section, wherein the exterior wall includes at least three mapping electrode openings and at least one irrigation port in fluid communication with the open interior region, wherein the exterior wall is conductive for delivering radio frequency (RF) energy for an RF ablation procedure;
a distal insert positioned within the tip section and separating the open interior region into a distal fluid reservoir and a proximal fluid reservoir, the distal insert defining a fluid conduit extending from the distal fluid reservoir to the proximal fluid reservoir, the distal insert having a peripheral surface with openings therein sized to receive the insulating elements, wherein the insulating elements electrically insulate the mapping electrodes from the distal insert, wherein at least one of the irrigation ports is in fluid communication with the distal fluid reservoir;

at least three mapping electrodes seated in the distal insert and aligned with the at least three mapping electrode openings;

at least three insulating elements surrounding the at least three mapping electrodes;

at least one insulated channel configured to electrically insulated wires extending from the at least three mapping electrodes from fluid within the open interior region.

20. The system of claim 19, wherein at least one of the irrigation ports is in fluid communication with the proximal fluid reservoir.

* * * * *